US012329558B2

(12) United States Patent
Yamamoto

(10) Patent No.: US 12,329,558 B2
(45) Date of Patent: Jun. 17, 2025

(54) X-RAY FLUOROSCOPIC IMAGING APPARATUS

(71) Applicant: SHIMADZU CORPORATION, Kyoto (JP)

(72) Inventor: Takaya Yamamoto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 230 days.

(21) Appl. No.: 18/258,261

(22) PCT Filed: Oct. 11, 2021

(86) PCT No.: PCT/JP2021/037605
§ 371 (c)(1),
(2) Date: Jun. 19, 2023

(87) PCT Pub. No.: WO2022/158056
PCT Pub. Date: Jul. 28, 2022

(65) Prior Publication Data
US 2024/0050052 A1    Feb. 15, 2024

(30) Foreign Application Priority Data
Jan. 25, 2021    (JP) .................... 2021-009541

(51) Int. Cl.
*A61B 6/00*    (2024.01)
*A61B 6/46*    (2024.01)
(Continued)

(52) U.S. Cl.
CPC .............. *A61B 6/463* (2013.01); *A61B 6/487* (2013.01); *A61B 6/5258* (2013.01); *G16H 30/40* (2018.01); *G16H 50/20* (2018.01)

(58) Field of Classification Search
CPC ....... A61B 34/20; A61B 1/00; A61B 1/00004; A61B 1/00011; A61B 1/00059;
(Continued)

(56) References Cited

U.S. PATENT DOCUMENTS

2019/0050981 A1*    2/2019    Song .................... A61B 5/7267

FOREIGN PATENT DOCUMENTS

JP    2017-185007 A    10/2017

OTHER PUBLICATIONS

Written Opinion by the International Searching Authority for PCT application No. PCT/JP2021/037605 dated Dec. 21, 2021.

* cited by examiner

*Primary Examiner* — Don K Wong
(74) *Attorney, Agent, or Firm* — Muir Patent Law, PLLC

(57) ABSTRACT

An X-ray fluoroscopic imaging apparatus includes an imaging unit, an X-ray image acquisition unit configured to acquire an X-ray image, a target distribution learning identification unit for outputting distribution of a target appearing in an X-ray image using a learning model, an image quality improvement processing unit, and a display unit. The image quality improvement processing unit is configured to switch, using a learning identification result by a target distribution learning identification unit, between a first image processing mode for performing image quality improvement processing on an X-ray image and a second image processing mode for performing image quality improvement processing on the X-ray image without using the learning identification result.

10 Claims, 9 Drawing Sheets

(51) Int. Cl.
*G16H 30/40* (2018.01)
*G16H 50/20* (2018.01)

(58) Field of Classification Search
CPC ............ A61B 2576/00; A61B 2576/02; A61B 2090/376; A61B 6/487; A61B 6/48; A61B 6/486; A61B 17/1703; A61B 6/5205; A61B 2090/364; A61B 8/4245; G06T 2207/10081; G06T 2207/20081; G06T 7/70; G06T 7/75; G06T 2207/10121; G06T 2207/10141
See application file for complete search history.

Modification

Modification

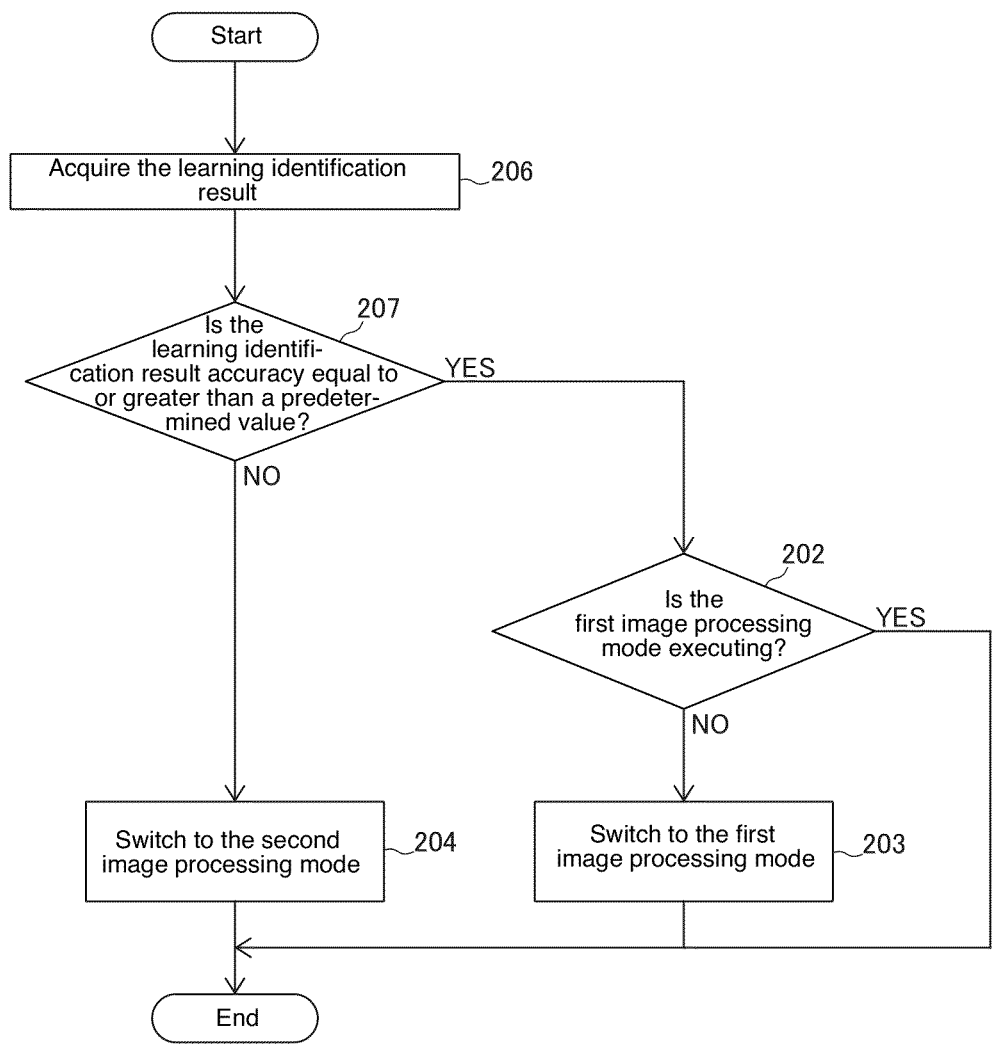

X-RAY FLUOROSCOPIC IMAGING APPARATUS

TECHNICAL FIELD

The present invention relates to an X-ray fluoroscopic imaging apparatus, more particularly to an X-ray fluoroscopic imaging apparatus for identifying a device introduced in a body of a subject, using a trained learning model.

BACKGROUND OF THE INVENTION

Conventionally, regarding an X-ray fluoroscopic imaging apparatus, there is known an X-ray fluoroscopic imaging apparatus for identifying a device introduced in a body of a subject, using a trained learning model. Such an X-ray fluoroscopic imaging apparatus is disclosed in, for example, Japanese Unexamined Patent Application Publication No. 2017-185007.

The X-ray fluoroscopic imaging apparatus disclosed in Japanese Unexamined Patent Application Publication No. 2017-185007 is provided with an irradiation unit, a radiation detector, an image generation unit, and a target object detector. The irradiation unit is configured to irradiate a subject with radiation. The radiation detector is configured to detect the radiation transmitted through the subject. The image generation unit is configured to generate a radiographic image based on the detection signal of the radiation detector. The target object detector is configured to identify a target object by image recognition from the radiographic image, based on the trained result data for image recognition acquired in advance by machine learning. In Japanese Unexamined Patent Application Publication No. 2017-185007, it is configured such that processing for emphasizing the identified target object is performed. Japanese Unexamined Patent Application Publication No. 2017-185007 discloses a configuration in which a device, such as, e.g., a guidewire, is identified as a target object and emphasized. In Japanese Unexamined Patent Application Publication No. 2017-185007, the target object detector is configured to identify the target object from a radiographic image in the form of a moving image.

PRIOR ART DOCUMENT

Patent Document

Patent Document 1: Japanese Unexamined Patent Application Publication No. 2017-185007

SUMMARY OF THE INVENTION

Problems to be Solved by the Invention

Here, although not disclosed in Japanese Unexamined Patent Application Publication No. 2017-185007, the trained learning model generated by performing machine learning affects the accuracy of identifying a target object (device) by the algorithm to be trained and the training data used for learning. Further, a device used in a surgical operation for introducing a device into a body of a patient has been improved in shape and the like in order to reduce the burden on the patient. Therefore, in the case of using a device (target) that has been improved to reduce the burden on a patient, depending on the difference between the shape of the target (device) in the training data used to train a learning model and the shape of the device (target) actually used in an actual surgical operation, the accuracy of identifying a target by a learning model may deteriorate. In this case, the accuracy of the identification result by the learning model may not be sufficient, which may result in erroneous detection of the target. In a case where the target is erroneously detected, there is a disadvantage in that a non-target part is emphasized when enhancement processing is performed based on the learning identification result output by the learning model, which may cause deterioration of the visibility of the target in the X-ray image. Therefore, in a configuration for identifying a target in an X-ray image using a learning model, there is a need for an X-ray fluoroscopic apparatus capable of suppressing a decrease in the visibility of a target due to a learning identification result output by a learning model. Note that the learning identification result includes a distribution (device position information) of a target to be output by a learning model.

The present invention has been made to solve the above-described problems and aims to provide an X-ray fluoroscopic imaging apparatus capable of suppressing a decrease in the visibility of a device due to a learning identification result output by a learning model.

Means for Solving the Problems

In order to attain the above-described object, an X-ray fluoroscopic imaging apparatus according to one aspect of the present invention includes:
  an imaging unit including an X-ray source for irradiating a subject with X-rays and an X-ray detector for detecting X-rays irradiated from the X-ray source;
  an X-ray image acquisition unit configured to acquire an X-ray image captured by the imaging unit;
  a target distribution learning identification unit configured to output distribution of a target appearing in the X-ray image using a trained learning model;
  an image quality improvement processing unit configured to perform image quality improvement processing for improving image quality of the X-ray image; and
  a display unit configured to display the X-ray image,
  wherein the image quality improvement processing unit is configured to switch between a first image processing mode for performing the image quality improvement processing on the X-ray image using a learning identification result by the target distribution learning identification unit and a second image processing mode for performing the image improvement processing mode on the X-ray image without using the learning identification result.

Effects of the Invention

In the X-ray fluoroscopic imaging apparatus according to the above-described aspect of the present invention, as described above, it is provided with an image quality improvement processing unit configured to switch a first image processing mode in which image quality improvement processing is performed on the X-ray image using a learning identification result and a second image processing mode in which image quality improvement processing is performed on the X-ray image without using the learning identification result. This makes it possible to switch between first image processing mode using a learning identification result using and a second image processing mode not using a learning identification result, depending on whether the accuracy of the learning identification result is high or low. That is, in a case where the accuracy of the learning identification result is high, the visibility of the target can be improved in the first image processing mode, and in a case where the accuracy of the learning identification result is low, the image quality improvement processing of the X-ray image can be performed in the second image processing mode, so that the visibility of the target can be suppressed from decreasing due to the learning identification result. Consequently, in the configuration in which the learning model is used to identify the device in the X-ray image, it is possible to prevent the deterioration of the visibility of the target due to the learning identification result output by the learning model.

BRIEF DESCRIPTION OF THE DRAWINGS

FIG. 9 is a flowchart describing image processing mode switching processing according to a modification.

EMBODIMENTS FOR CARRYING OUT THE INVENTION (Configuration of X-Ray Fluoroscopic Imaging Apparatus)

Figure 1:
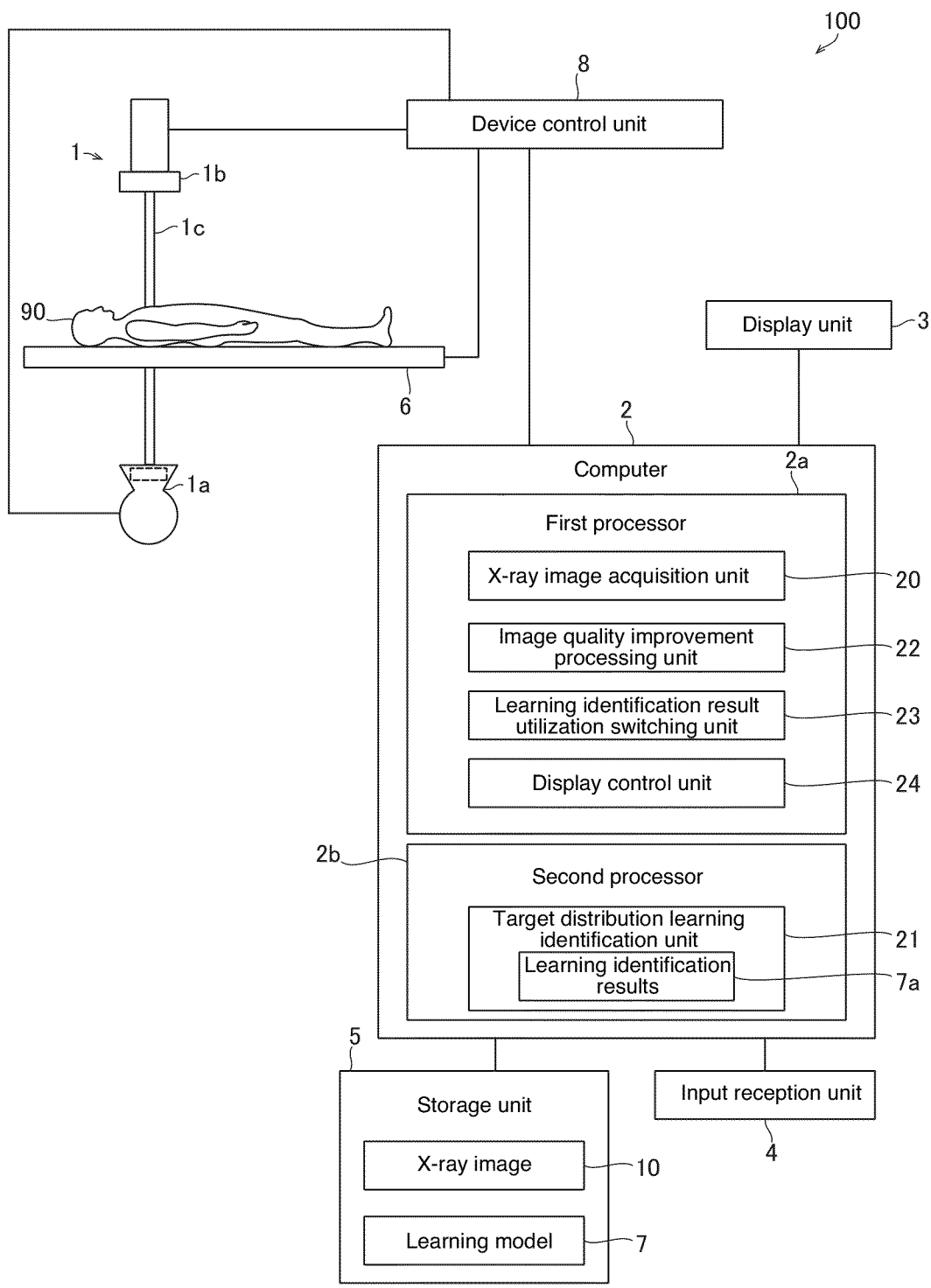
FIG. 1 is a diagram showing an entire configuration of an X-ray fluoroscopic imaging apparatus according to one embodiment.

Referring to FIG. 1, a configuration of an X-ray fluoroscopic imaging apparatus 100 according to one embodiment of the present invention will be described.

As shown in FIG. 1, an X-ray fluoroscopic imaging apparatus 100 according to this embodiment is provided with an imaging unit 1, a computer 2, a display unit 3, an input reception unit 4, a storage unit 5, a top board 6, and a device control unit 8. In this embodiment, the X-ray fluoroscopic imaging apparatus 100 images a subject 90 as an object. The X-ray fluoroscopic imaging apparatus 100 is used, for example, in manipulation for treating a stenotic site of a blood vessel of the subject 90 using a device 80 (see FIG. 2). The device 80 includes at least one of a catheter, a stent, and a guidewire introduced into the blood vessel of the subject 90.

The imaging unit 1 includes an X-ray source 1a, an X-ray detector 1b, and an arm 1c to which the X-ray source 1a and the X-ray detector 1b are arranged to face each other.

The X-ray source 1a is configured to irradiate the subject 90 with X-rays. Specifically, the X-ray source 1a emits X-rays when a voltage is applied by a drive unit (not shown). The X-ray source 1a has a collimator capable of adjusting the irradiation field which is an irradiation range of X-rays. In this embodiment, the X-ray source 1a is attached to one tip end of the arm 1c.

The X-ray detector 1b is configured to detect X-rays emitted from the X-ray source 1a. In this embodiment, the X-ray detector 1b is attached to the other tip end of the arm 1c. That is, the X-ray detector 1b is arranged on the side opposite of the X-ray source 1a with the top board 6 interposed therebetween. The X-ray detector 1b is configured to detect X-rays. The X-ray detector 1b is, for example, an FPD (Flat Panel Detector). The X-ray detector 1b is configured to detect X-rays transmitted through the subject and provide a detection signal based on the detected X-rays.

The computer 2 is composed of a first processor 2a, such as, e.g., a CPU (Central Processing Unit), a GPU (Graphics Processing Unit), and an FPGA (Field-Programmable Gate Array) configured for image processing, a second processor 2b, such as, e.g., a CPU, a GPU, and an FPGA configured for image processing, and a ROM (Read Only Memory) and a RAM (Random Access Memory).

As shown in FIG. 1, the first processor 2a includes an X-ray image acquisition unit 20 and an image quality improvement processing unit 22. In this embodiment, the first processor 2a further includes a learning identification result utilization switching unit 23. Further, in this embodiment, the first processor 2a further includes a display control unit 24. The X-ray image acquisition unit 20, the image quality improvement processing unit 22, the learning identification result utilization switching unit 23, and the display control unit 24 are configured in a software manner as functional blocks realized by the first processor 2a executing various programs. The X-ray image acquisition unit 20, the image quality improvement processing unit 22, the learning identification result utilization switching unit 23, and the display control unit 24 may be configured by hardware with a dedicated processor (processing circuit).

The second processor 2b is provided separately from the first processor 2a. The second processor 2b includes a target distribution learning identification unit 21. The target distribution learning identification unit 21 is configured in a software manner as a functional block realized by the second processor 2b executing various programs. The target distribution learning identification unit 21 may be configured as hardware by a dedicated processing circuit.

The X-ray image acquisition unit 20 is configured to acquire an X-ray image 10 captured by the imaging unit 1. In this embodiment, the X-ray image acquisition unit 20 is configured to acquire the X-ray image 10 as a moving image. That is, the X-ray image acquisition unit 20 is configured to acquire the X-ray image 10 for each frame.

The target distribution learning identification unit 21 is configured to output the distribution of the target appearing in the X-ray image 10 using a trained learning model 7. In this embodiment, the target includes at least one of the device 80, a blood vessel, and a bone appearing in the X-ray image 10. That is, in this embodiment, the target includes at least any one of a stent, a guidewire, a catheter, a blood vessel, and a bone. Note that in this embodiment, an example in which the target is the device 80 will be described. Further, the distribution of the target is the position information on the device 80. The learning model 7 is generated in advance by learning to identify the device 80 appearing in the X-ray image 10. Further, the learning model 7 is stored in the storage unit 5.

Further, the image quality improvement processing unit 22 is configured to perform image quality improvement processing for improving the image quality of the X-ray image 10. Further, the learning identification result utilization switching unit 23 is configured to switch whether to use the learning identification result 7a of the device 80 by the target distribution learning identification unit 21. Further, the display control unit 24 is configured to display an image processing mode together with the X-ray image 10. The detailed configurations of the target distribution learning identification unit 21, the image quality improvement processing unit 22, the learning identification result utilization switching unit 23, and the display control unit 24 will be described later. Note that the learning identification result 7a of the device 80 includes the position information on the device 80 appearing in the X-ray image 10.

The display unit 3 is configured to display the X-ray image 10. In this embodiment, the display unit 3 is configured to show an X-ray image 10a (see FIG. 3) as a moving mage after being subjected to image quality improvement processing or an enhanced image 11a (see FIG. 2) as a moving image after being subjected to image quality improvement processing. The display unit 3 is a monitor provided in the X-ray fluoroscopic imaging apparatus 100.

The input reception unit 4 is configured to accept an operation input by the operator. The input reception unit 4 includes, for example, an input device, such as, e.g., a mouse and a keyboard.

The storage unit 5 is configured to store the X-ray image 10 acquired by the X-ray image acquisition unit 20, the X-ray image 10a after being subjected to image quality improvement processing, the enhanced image 11 (see FIG. 2) in which the device 80 in the X-ray image 10 is emphasized, the enhanced image 11a after being subjected image quality improvement processing, and the like. Further, the storage unit 5 is configured to store various programs to be executed by the first processor 2a and the second processor 2b. The storage unit 5 includes a non-volatile memory, such as, e.g., an HDD (Hard Disk Drive) and an SSD (Solid State Drive).

As shown in FIG. 1, the top board 6 is formed in a rectangular flat plate shape in plan view. The subject 90 is placed on the top board 6 such that the head-foot direction of the subject 90 is in a direction along the long side of the rectangle, and the left-right direction of the subject 90 is in a direction along the short side of the rectangle.

The top board 6 is provided with a moving mechanism (not shown). The X-ray fluoroscopic imaging apparatus 100 can image the subject while changing the relative position between the top board 6 and the imaging unit 1 by moving the top board 6 in the longitudinal direction by a moving mechanism.

The device control unit 8 is configured to control the X-ray fluoroscopic imaging apparatus 100. Specifically, the device control unit 8 is configured to perform control of the X-ray source 1a, the arm 1c, the top board 6, and the like. The device control unit 8 is configured to control the dose of the X-rays output from the X-ray source 1a by controlling the X-ray source 1a based on the input of the operator.

As shown in FIG. 1, the operator (medical doctor, technician, etc.) captures a plurality of X-ray images 10 while administering a contrast agent to the subject 90 placed on the top board 6 and changing the relative position between the imaging unit 1 and the top board 6. Further, the operator captures the X-ray image 10 when moving the device 80 introduced into the blood vessel of the subject 90 to a predetermined position. In this embodiment, the operator introduces the device 80 to the blood vessel of the heart of the subject 90. Here, in order to reduce the exposure dose of the subject 90, it is preferable to reduce the dose of the X-rays emitted from the X-ray source 1a.

Figure 2:
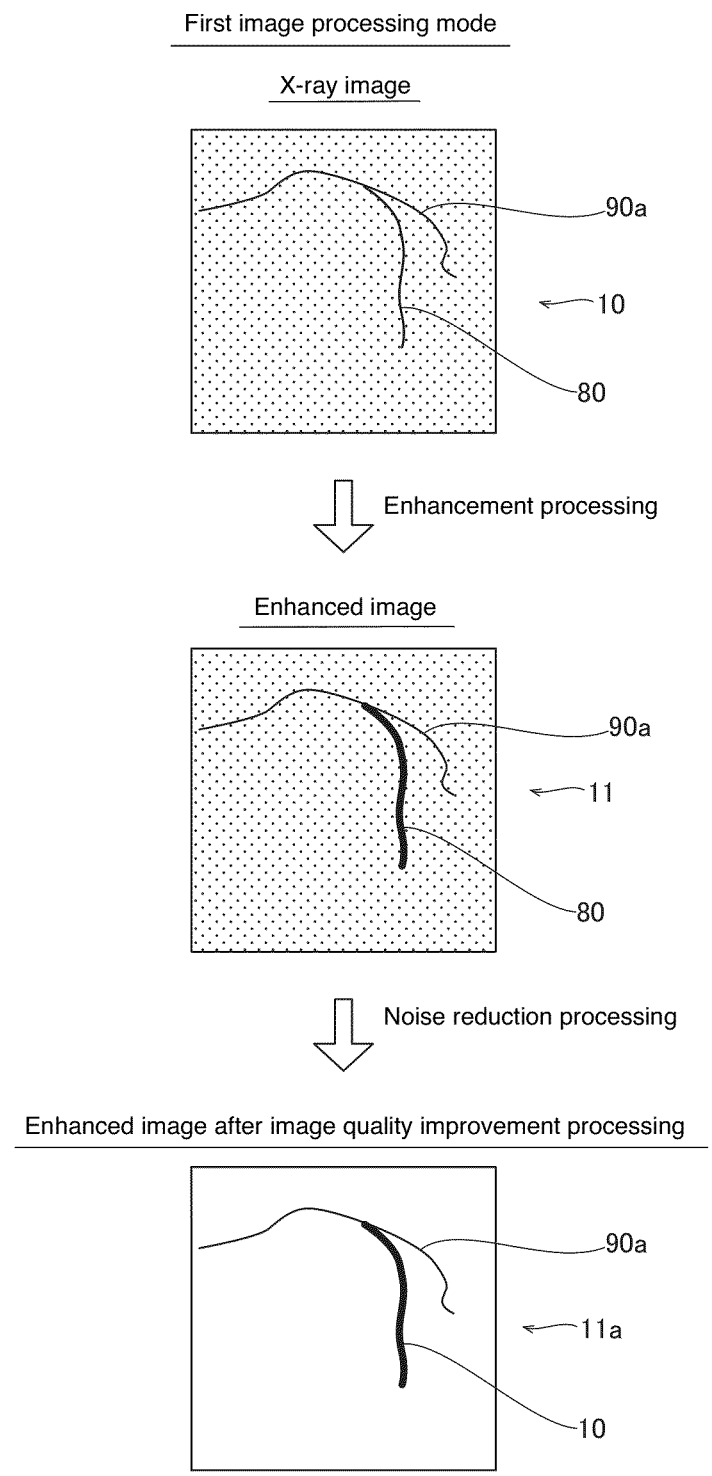
FIG. 2 is a schematic diagram showing a configuration in which an image quality improvement processing unit according to one embodiment generates an enhanced image after image quality improvement processing in a first image processing mode.

However, when the dose of the X-rays is reduced, noise occurs in the X-ray image 10 as shown in FIG. 2. When noise is generated in the X-ray image 10, the visibility of the device 80 in the X-ray image 10 deteriorates. Therefore, it is sometimes difficult for an operator to perform a surgical operation by using the device 80. Note that in FIG. 2, the noise in the X-ray image 10 is represented by hatching.

(First Image Processing Mode)

Therefore, in this embodiment, as shown in FIG. 2, the image quality improvement processing unit 22 is configured to improve the visibility of the device 80 by performing image quality improvement processing for improving the image quality of the X-ray image 10. In this embodiment, the image quality improvement processing includes at least noise reduction processing.

Further, as shown in FIG. 2, the X-ray image 10 may include a human body structure 90a of the subject 90. In this instance, it may be difficult to distinguish between the device 80 and the human body structure 90a. Note that the human body structure 90a is, for example, a blood vessel other than a blood vessel to which the device 80 is introduced among blood vessels of the heart. Note that the human body structure 90a includes, in addition to blood vessels, an edge of an organ such as a heart, an edge of a diaphragm, and the like.

Therefore, the image quality improvement processing unit 22 is configured to generate, in the first image processing mode, an enhanced image 11 in which enhancement processing of the device 80 in the X-ray image 10 has been performed. In this embodiment, the image quality improvement processing unit 22 identifies the device 80 and the background portion other than the device 80 by using a learning identification result 7a when performing the enhancement processing. Then, the image quality improvement processing unit 22 emphasizes the device 80 by performing the processing for increasing the pixel value on the device 80. Note that in this specification, the increase in the pixel value of the device 80 is represented by changing the thickness of the line depicting the device 80. That is, as the pixel value of the device 80 increases, the device 80 is shown to be thicker.

Further, in this embodiment, the image quality improvement processing unit 22 is configured to perform noise reduction processing on the enhanced image 11 in the first image processing mode using the learning identification result 7a.

In the first image processing mode, the image quality improvement processing unit 22 generates an enhanced image 11a after image quality improvement processing by performing noise reduction processing on the enhanced image 11. In this embodiment, the image quality improvement processing unit 22 is configured to perform processing using at least a recursive filter that adds a pixel value of a predetermined pixel in each frame of the X-ray image 10, as noise reduction processing. In the processing using a recursive filter, the pixel value of the predetermined pixel in each frame of the X-ray image 10 is weighted and added. However, like this embodiment, for example, in a surgical operation for introducing the device 80 into a blood vessel of a heart, the position where the device 80 appears differs for each frame.

Therefore, in this embodiment, when performing the processing using a recursive filter, the device 80 is aligned for each frame, and a pixel to be added is aligned.

The enhanced image 11a after image quality improvement processing has high accuracy of the positioning of the device 80 for each frame when the learning identification result 7a has sufficient accuracy. Therefore, the visibility of the device 80 is higher than that of the device 80 in the X-ray image 10a (see FIG. 3) after image quality improvement processing in the second image processing mode, which will be described later. For this reason, in this embodiment, the first image processing mode is set as a normal image processing mode.
(Second Image Processing Mode)

Here, when the accuracy of the discrimination result of the device 80 by the learning identification result 7a is low, it may be erroneously detected that the blood vessel other than the device 80 is the device 80. In this case, in some frames of the X-ray image 10 as a moving image, a blood vessel or the like existing at a position different from the position of the device 80 may be emphasized. Further, when the accuracy of the discrimination result of the device 80 by the learning identification result 7a is low, the accuracy of the alignment of the device 80 also decreases when performing the noise reduction processing using a recursive filter on the X-ray image 10 as a moving image. In this case, as a result of performing the processing using a recursive filter, a shift occurs in the position of the pixel to be added, and thus an afterimage of the device 80 occurs. Therefore, the visibility of the device 80 in the X-ray image 10 as a moving image deteriorates.

Figure 3:
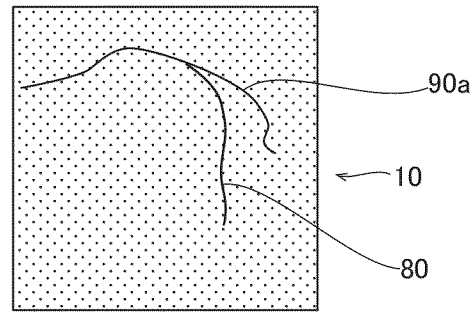
FIG. 3 is a schematic diagram showing a configuration in which an image quality improvement processing unit according to one embodiment generates an X-ray image after image quality improvement processing in a second image processing mode.
Figure 3:
Figure 3:
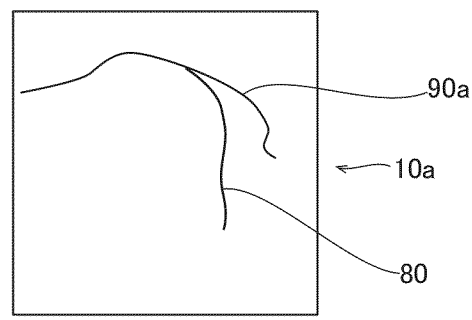

Therefore, in this embodiment, as shown in FIG. 3, the image quality improvement processing unit 22 is configured to perform noise reduction processing on the X-ray image 10 in which enhancement processing is not performed, in the second image processing mode that does not use the learning identification result 7a. In other words, in the second image processing mode, the image quality improvement processing unit 22 performs noise reduction processing on the X-ray image 10 acquired by the X-ray image acquisition unit 20. Specifically, in the second image processing mode, the image quality improvement processing unit 22 aligns the device 80 in each frame by pattern matching. With this, in the processing using a recursive filter, the noise is reduced while suppressing the generation of an afterimage. Note that in a case where the dose of the X-rays is low, even if the image quality improvement processing is performed in the second image processing mode, the contrast of the X-ray image 10 after image quality improvement processing may be low. In this case, it is conceivable for the operator to perform an operation input for increasing the dose of the X-rays. Therefore, the device control unit 8 is configured to accept an operation input for increasing the dose of X-rays emitted from the X-ray source 1a.
(Switching Image Processing Mode)

For some medical doctors, even a slight decrease in the visibility of the device 80 due to the accuracy of the learning identification result 7a may not be acceptable. Further, according to a preference of a medical doctor or the like, there is a case where it is desired to display the X-ray image 10a subjected to the image quality improvement processing in the second image processing mode from the beginning.

Therefore, in this embodiment, the image quality improvement processing unit 22 is configured to switch between the first image processing mode for performing the image quality improvement processing on the X-ray image 10 using the learning identification result 7a and the second image processing mode for performing the image quality improvement processing on the X-ray image 10 without using the learning identification result 7a. Specifically, the image quality improvement processing unit 22 is configured to switch between the first image processing mode and the second image processing mode when the learning identification result utilization switching unit 23 switches the image processing mode. In this embodiment, the learning identification result utilization switching unit 23 is configured to switch between the first image processing mode and the second image processing mode, based on an input by the input reception unit 4 (see FIG. 1).

Figure 4:
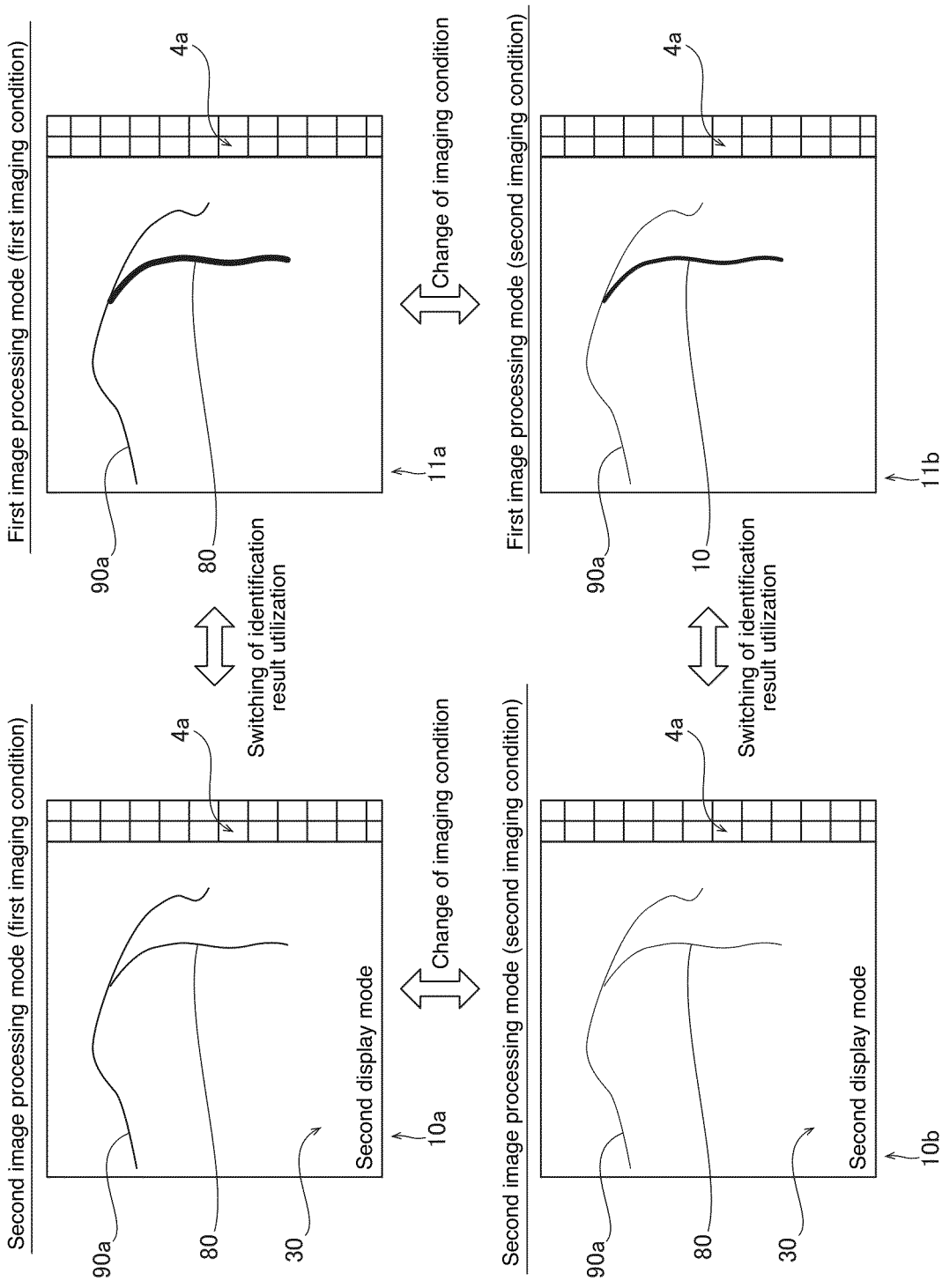
FIG. 4 is a schematic diagram describing switching between a first image processing mode and a second image processing mode.

Specifically, as shown in FIG. 4, the learning identification result utilization switching unit 23 is configured to switch between the first image processing mode and the second image processing mode, based on an operation input inputted by the medical doctor or the like operating the switching button 4a by the input reception unit 4. Note that the switching button 4a is a button displayed on the X-ray image 10a after the image quality improvement processing or a GUI (Graphical User Interface) to be displayed with the enhanced image 11a after the image quality improvement processing, on the display unit 3.

Further, in this embodiment, the target distribution learning identification unit 21 is configured to perform processing for identifying a target (device 80) both in the first image processing mode and the second image processing mode. That is, although the learning identification result 7a is not used in the second image processing mode, the target distribution learning identification unit 21 continuously outputs the learning identification result 7a even in the second image processing mode.
(Display Image Processing Mode)

As shown in FIG. 4, in this embodiment, the display control unit 24 is configured to cause the display unit 3 to display that it is in the second image processing mode together with the X-ray image 10 at least during the execution of the second image processing mode. Specifically, the display control unit 24 is configured to cause the display unit 3 to display a message 30 indicating that it is in the second image processing mode, together with the X-ray image 10a or the X-ray image 10b when displaying the X-ray image 10a or the X-ray image 10b generated in the second image processing mode on the display unit 3.

Note that in this embodiment, as shown in FIG. 4, the first image processing mode is set as a normal image processing mode. Therefore, the display control unit 24 is configured not to display that it is in the first image processing mode on the display unit 3 during the execution of the first image processing mode.
(Switching Between Imaging Position and Imaging Condition)

The X-ray fluoroscopic imaging apparatus 100 is configured to switch the imaging positions or the imaging conditions by accepting an operation input by a medical doctor by the input reception unit 4. The imaging condition includes, for example, the dose of X-rays output from the X-ray source 1a, the arrangement of the X-ray source 1a, and the X-ray detector 1b by the arm 1c.

Here, the medical doctor or the like intentionally switches between the first image processing mode and the second image processing mode by operating the switching button 4a. For example, in a case where the image processing mode is again switched to the second image processing mode which is an image processing mode before switching when a medical doctor or the like switched between the first image processing mode and the second image processing mode, it is required to switch back to the second image processing mode, which causes the doctor or the like to perform an unnecessary operation.

Thus, as shown in FIG. 4, in this embodiment, the learning identification result utilization switching unit 23 is configured to maintain the currently executing first or second image processing mode even when at least one of the imaging site and the imaging condition is changed.

In the example shown in FIG. 4, the case in which the medical doctor or the like has switched the imaging condition is shown. Specifically, the example shown in FIG. 4 shows the case in which a medical doctor or the like has changed the dose of X-rays. In FIG. 4, an example is shown in which the second imaging condition is lower than the first imaging condition in the dose of X-rays. In the second imaging condition, since the dose of X-rays is lower, the device 80 and the human body structure 90a appearing in the X-ray image 10b after the image quality improvement processing acquired in the second imaging condition are smaller in the pixel value than the X-ray image 10a after the image quality improvement processing captured by the first imaging condition. In FIG. 4, the device 80 and the human body structure 90a appearing in the X-ray image 10b captured under the second imaging condition are illustrated with a thin line so that it is expressed that the pixel value of the device 80 and the human body structure 90a appearing in the X-ray image 10a captured under the first imaging condition is small.

Also for the device 80 and the human body structure 90a appearing in the enhanced image 11b after the image quality improvement process acquired under the second imaging condition, they are illustrated with a thinner line than the enhanced image 11a after the image quality improvement captured under the first condition, so that it is expressed that the pixel value is smaller.

Figure 5:
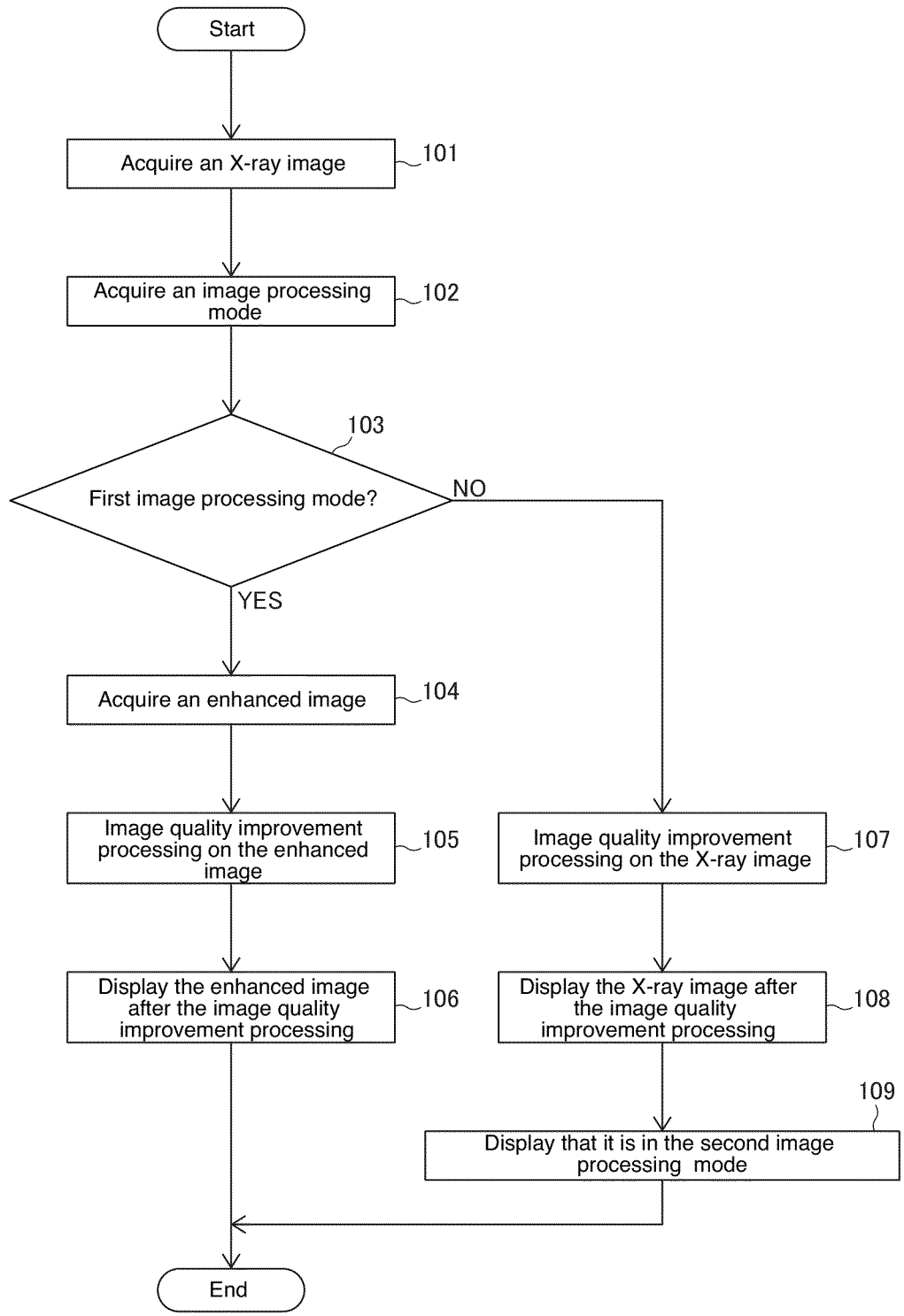
FIG. 5 is a flowchart describing image quality improvement processing according to one embodiment.

Next, the image quality improvement processing of the X-ray image 10 by the X-ray fluoroscopic imaging apparatus 100 will be described with reference to FIG. 5. Note that the image quality improvement processing of the X-ray image 10 by the X-ray fluoroscopic imaging apparatus 100 is performed each time for acquiring each frame of the X-ray image 10.

In Step 101, the X-ray image acquisition unit 20 acquires the X-ray image 10. Specifically, the X-ray image acquisition unit 20 acquires the X-ray image 10 as a moving image for each frame.

In Step 102, the learning identification result utilization switching unit 23 acquires the currently executing image processing mode.

In Step 103, the learning identification result utilization switching unit 23 determines whether the currently executing image processing mode is the first image processing mode. In a case where the currently executing image processing mode is the first image processing mode, the processing proceeds to Step 104. In a case where the currently executing image processing mode is the second image processing mode, the processing proceeds to Step 107.

In Step 104, the image quality improvement processing unit 22 acquires the enhanced image 11 by highlighting the device 80 in the X-ray image 10 using the learning identification result 7a.

In Step 105, the image quality improvement processing unit 22 performs image quality improvement processing on the enhanced image 11. Specifically, the image quality improvement processing unit 22 performs noise reduction processing on the enhanced image 11 to acquire the enhanced image 11a after the image quality improvement processing.

In Step 106, the display control unit 24 causes the display unit 3 to display the enhanced image 11a after the image quality improvement processing.

When the processing has proceeded from Step 102 to Step 107, in Step 107, the image quality improvement processing unit 22 performs image quality improvement processing on the X-ray image 10. Specifically, the image quality improvement processing unit 22 performs noise reduction processing on the X-ray image 10 to acquire the X-ray image 10a after the image quality improvement processing.

In Step 108, the display control unit 24 causes the display unit 3 to display the X-ray image 10a after the image quality improvement processing.

In Step 109, the display control unit 24 causes the display unit 3 to display the second image processing mode. Specifically, the display control unit 24 causes the display unit 3 to display the message 30 indicating that it is in the second image processing mode together with the X-ray image 10a after the image quality improvement processing. Thereafter, the processing ends.

Figure 6:
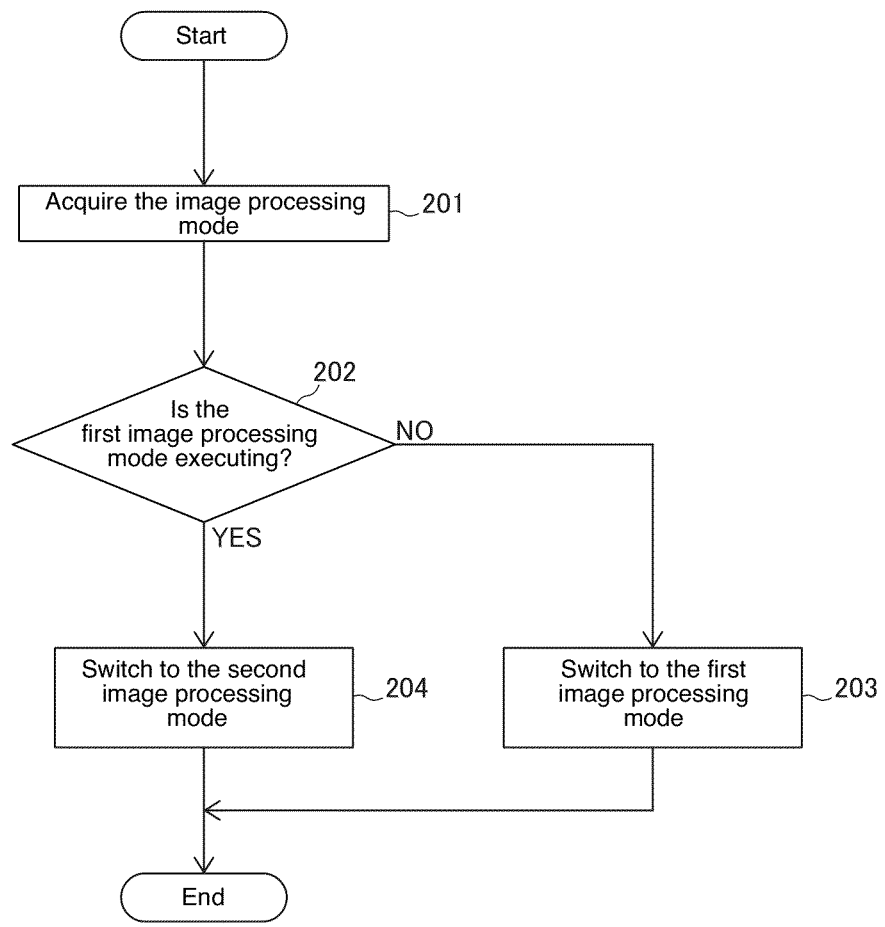
FIG. 6 is a flowchart describing image processing mode switching processing according to one embodiment.

Next, referring to FIG. 6, the processing in which the X-ray fluoroscopic imaging apparatus 100 switches between the first image processing mode and the second image processing mode will be described. The following processing is started when an operator operates the switching button 4a of the input reception unit 4.

In Step 201, the learning identification result utilization switching unit 23 acquires the image processing mode.

In Step 202, the learning identification result utilization switching unit 23 determines whether the first image processing mode is being executed. When the first image processing mode is not being executed, the processing proceeds to Step 203. When the first image processing mode is being executed, the processing proceeds to Step 204.

In Step 203, the learning identification result utilization switching unit 23 switches the image processing mode to the first image processing mode. Thereafter, the processing ends.

When the processing has proceeded from Step 202 to Step 204, in Step 204, the learning identification result utilization switching unit 23 switches the image processing mode to the second image processing mode. Thereafter, the processing ends.

Effectiveness of this Embodiment

In this embodiment, the following advantages can be acquired.

In this embodiment, as described above, the X-ray fluoroscopic imaging apparatus 100 is provided with an imaging unit 1 including the X-ray source 1a for irradiating the object (subject 90) with X-rays, and an X-ray detector 1b for detecting the X-rays irradiated from the X-ray source 1a, the X-ray image acquisition unit 20 for acquiring the X-ray image 10 captured by the imaging unit 1, the target distribution learning identification unit 21 for outputting the distribution (position information on the device 80) of the target appearing in the X-ray image 10 using the trained learning model 7, the image quality improvement processing unit 22 for improving the image quality of the X-ray image 10, and the display unit 3 for displaying the X-ray image 10. The image quality improvement processing unit 22 is configured to be capable of switching between the first image processing mode in which the image quality improvement processing is performed on the X-ray image 10 using the learning identification result 7a and the second image processing mode in which the image quality improvement processing is performed on the X-ray image 10 without using the learning identification result 7a.

This makes it possible to switch between the first image processing mode using the learning identification result 7a using and the second image processing mode without using the learning identification result 7a, depending on whether the accuracy of the learning identification result 7a is higher or lower. That is, when the accuracy of the learning identification result 7a is high, the visibility of the target (device 80) can be improved by the first image processing mode, and when the accuracy of the learning identification result 7a is low, it is possible to suppress the deterioration of the visibility of the target due to the learning identification result 7a by performing the image quality improvement processing of the X-ray image 10 by the second image processing mode. Consequently, in the configuration of identifying the target in the X-ray image 10 using the learning model 7, it is possible to suppress the deterioration of the visibility of the target due to the learning identification result 7a output by the learning model 7.

Further, in the above-described embodiment, the following effects can be obtained by the following configuration.

That is, in this embodiment, as described above, the image quality improvement processing includes at least noise reduction processing, and the image quality improvement processing unit 22 is configured to perform the noise reduction processing on the enhanced image 11 in which the target (device 80) in the X-ray image 10 is subjected to the enhancement processing in the first image processing mode using the learning identification result 7a, and perform the noise reduction processing on the X-ray image not subjected to the enhancement processing in the second image processing mode. As a result, in the first image processing mode, by performing the enhancement processing for enhancing the device 80 and then performing the noise reduction processing, the visibility of the device 80 can be further improved than the image acquired by the image processing improvement processing by the second image processing mode without using the learning identification result 7a. Further, even in the second image processing mode in which the accuracy of the learning identification result 7a is low and the learning identification result 7a is not used, by performing the noise reduction processing, it is possible to improve the visibility of the device 80 than the X-ray image 10 not subjected to the noise reduction processing. Consequently, it is possible to improve the visibility of the device 80 than the X-ray image 10 not subjected to the noise reduction processing while suppressing the deterioration of the visibility of the device by the learning identification result 7a.

Further, in this embodiment, as described above, the display control unit is further provided. The display control unit is configured to cause the display unit 3 to display that it is in the second image processing mode together with the X-ray image 10 during the execution of at least the second image processing mode, and not to display that it is in the first image processing mode during the execution of the first image processing mode. With this, since it is displayed on the display unit 3 that it is in the second image processing mode only during the execution of the second image processing mode, it is possible to make the operator easily grasp the state in which the learning identification result 7a by the learning model 7 is not used.

Further, in this embodiment, as described above, the learning identification result utilization switching unit 23 is further provided. The learning identification result utilization switching unit 23 is configured to switch whether to use the learning identification result 7a by the target distribution learning identification unit 21. With this configuration, the first image processing mode and the second image processing mode can be easily switched by switching whether the learning identification result 7a is used by the learning identification result utilization switching unit 23.

Further, in this embodiment, as described above, the learning identification result utilization switching unit 23 is configured to maintain the first image processing mode or the second that are being executed even in a case where at least one of the imaging site and the imaging condition has been changed. With this, the executing image processing mode is maintained, and therefore, even in the case where at least one of the imaging site and the imaging condition is changed, it is possible to suppress that the image processing mode intentionally changed by the operator from returning to the image processing mode before change. Consequently, in a case where at least one of the imaging site and the imaging condition is changed, as compared with the configuration in which the image processing mode is returned to the standard image processing mode, it is possible to suppress the operator from performing unnecessary operations, and therefore, it is possible to improve the convenience (usability) of the operator.

Further, this embodiment, as described, the input reception unit 4 for accepting an operation input of the operator is further provided. The learning identification result utilization switching unit 23 is configured to switch between the first image processing mode and the second image processing mode based on the input by the input reception unit 4. With this, it is possible for the operator to switch between the first image processing mode and the second image processing mode at an arbitral timing, which can further improve the convenience (usability) of the operator.

Also, in this embodiment, as described above, it is provided with the first processor 2a including the X-ray image acquisition unit 20, the image quality improvement processing unit 22, and the learning identification result utilization switching unit 23, and the second processor 2b are provided separately from the first processor 2a, the second processor 2b including the target distribution learning identification unit 21. The X-ray image acquisition unit 20 is configured to acquire the X-ray image 10 as a moving image. The target distribution learning identification unit 21 is configured to perform the processing for identifying the device 80 either in the first image processing mode and the second image processing mode. With this, the processing of acquiring the learning identification result 7a of the device 80 and the processing of improving the image quality of the X-ray image 10 are executed by the different processors. Therefore, unlike the configuration in which the X-ray image acquisition unit 20, the image quality improvement processing unit 22, the learning identification result utilization switching unit 23, and the target distribution learning identification unit 21 are included in one processor, even if the processing of identifying the target (device 80) is performed in either the first image processing mode or the second image processing mode, it is possible to suppress an increase in the processing load in the processor. Further, by the target distribution learning identification unit 21 included in the second processor 2b, the second image processing mode can be continuously acquired even during the execution of the learning identification result. Therefore, as compared with the configuration in which the learning identification result 7a is not acquired during the execution of the second image processing mode, even in a case where the second image processing mode is switched to the first image processing mode, it is possible to suppress an increase in the time required for switching the image quality improvement processing. Consequently, it is particularly useful to apply the present invention to the X-ray image 10 as a moving image.

Further, in this embodiment, as described above, the image quality improvement processing unit 22 is configured to perform the processing using a recursive filter, as noise reduction processing, that adds at least the pixel value of the predetermined pixel in each frame of the X-ray image 10. With this, in the first image processing mode, the learning identification result 7a of the device 80 can be used when performing the processing using a recursive filter. Consequently, the position of the device 80 can be acquired in each image in detail, and therefore, it is possible to reduce the afterimage of the device 80 generated by the recursive filter processing. Further, in the second image processing mode, since it is possible to suppress the execution of the recursive filter processing using the device 80 appearing at a position that does not actually exist by the learning identification result 7a, the noise reduction effect by the recursive filter processing can be improved.

In this embodiment, as described above, the target includes at least one of the stent, the guidewire, the catheter, the blood vessel, and the bone appearing in the X-ray image 10. With this, it is possible to perform the image quality improvement processing in the first image processing mode or the second image processing mode, on the target desired by the operator, out of the stent, the guidewire, the catheter, the blood vessel, and the bone appearing in the X-ray image 10. As a result, since it is possible to perform the image quality improvement processing in a desired image processing mode on a desired object, it is possible to improve the convenience (useability) of the operator.

Modifications

It should be noted that the embodiments disclosed in this disclosure are illustrative and not restrictive in all respects. The scope of the present invention is indicated by claims rather than by the above-described descriptions of the embodiments, and includes all modifications within the meaning and scope equivalent to the claims.

For example, in the above-described embodiment, an example is shown in which the learning identification result utilization switching unit 23 switches whether to use the learning identification result 7a based on the input of the input reception unit 4, but the present invention is not limited thereto. In the present invention, for example, like the modification shown in FIG. 7, the learning identification result utilization switching unit 120 may be configured to switch whether to use the learning identification result 7a based on the learning identification result 7a.

Figure 7:
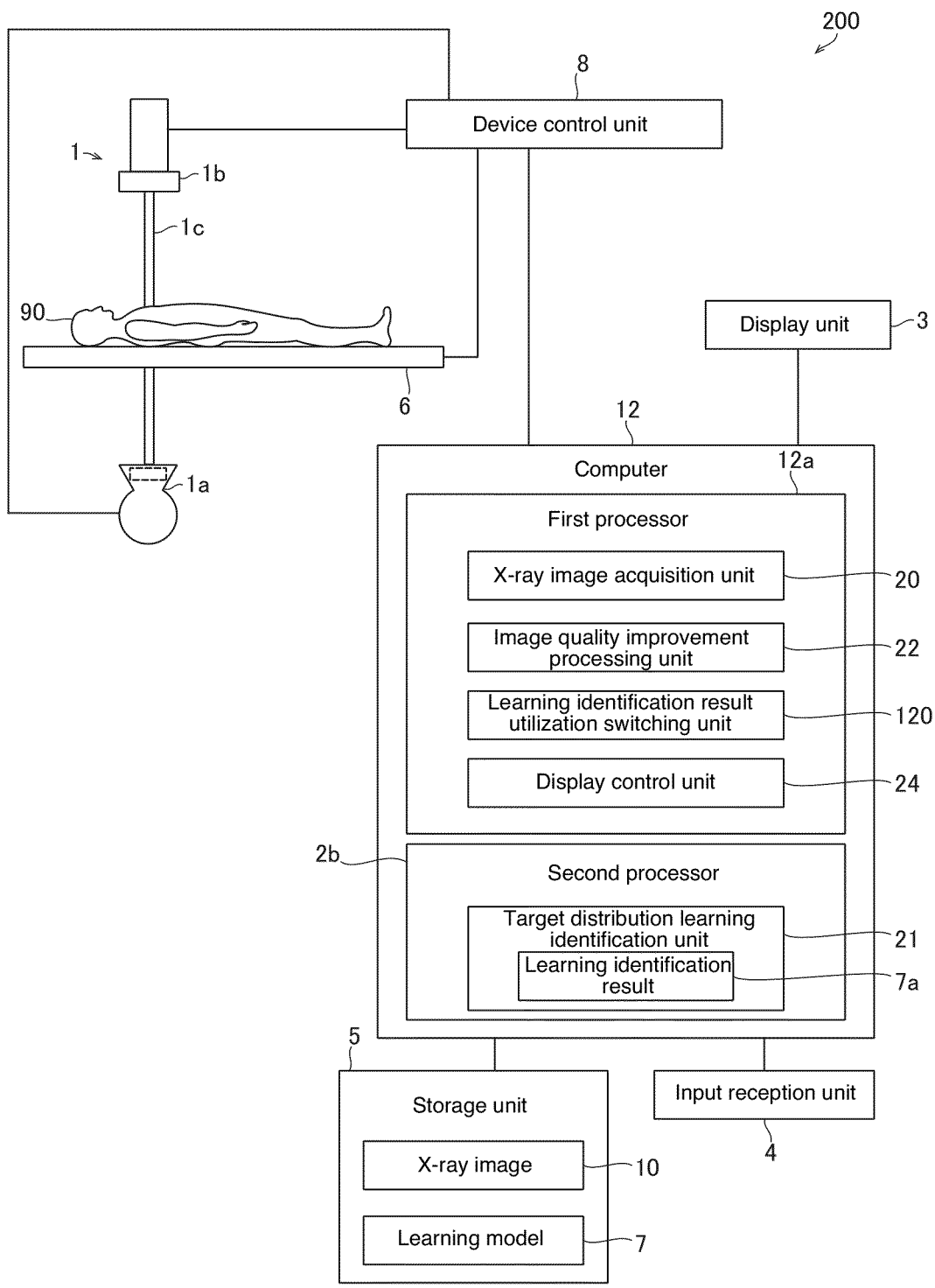
FIG. 7 is a diagram showing an entire configuration of an X-ray fluoroscopic imaging apparatus according to a modification.

The X-ray fluoroscopic imaging apparatus 200 of the modification shown in FIG. 7 differs from the X-ray fluoroscopic imaging apparatus 100 of the above-described embodiment in that it is provided with the computer 12 instead of the computer 2. The computer 12 differs from the computer 2 in the above-described embodiment in that it includes a first processor 12a instead of the first processor 2a. Further, the first processor 12a differs from the first processor 2a according to the above-described embodiment in that the learning identification result utilization switching unit 120 is provided instead of the learning identification result utilization switching unit 23.

In the modification, the learning identification result utilization switching unit 120 is configured to switch between the first image processing mode and the second image processing mode, based on the learning identification result 7a output from the learning model 7. Specifically, the learning identification result utilization switching unit 120 is configured to switch between the first image processing mode and the second image processing mode, based on the accuracy of the learning identification result 7a. More specifically, the learning identification result utilization switching unit 120 is configured to set to the first image processing mode when the accuracy of the learning identification result 7a is equal to or higher than the threshold and set to the second image processing mode when the accuracy of the identification result 7a is lower than the threshold. Note that in this embodiment, the accuracy of the learning identification result 7a includes a numerical value indicating the probability of the output result output together with the learning identification result 7a by the learning model 7.

Figure 8:
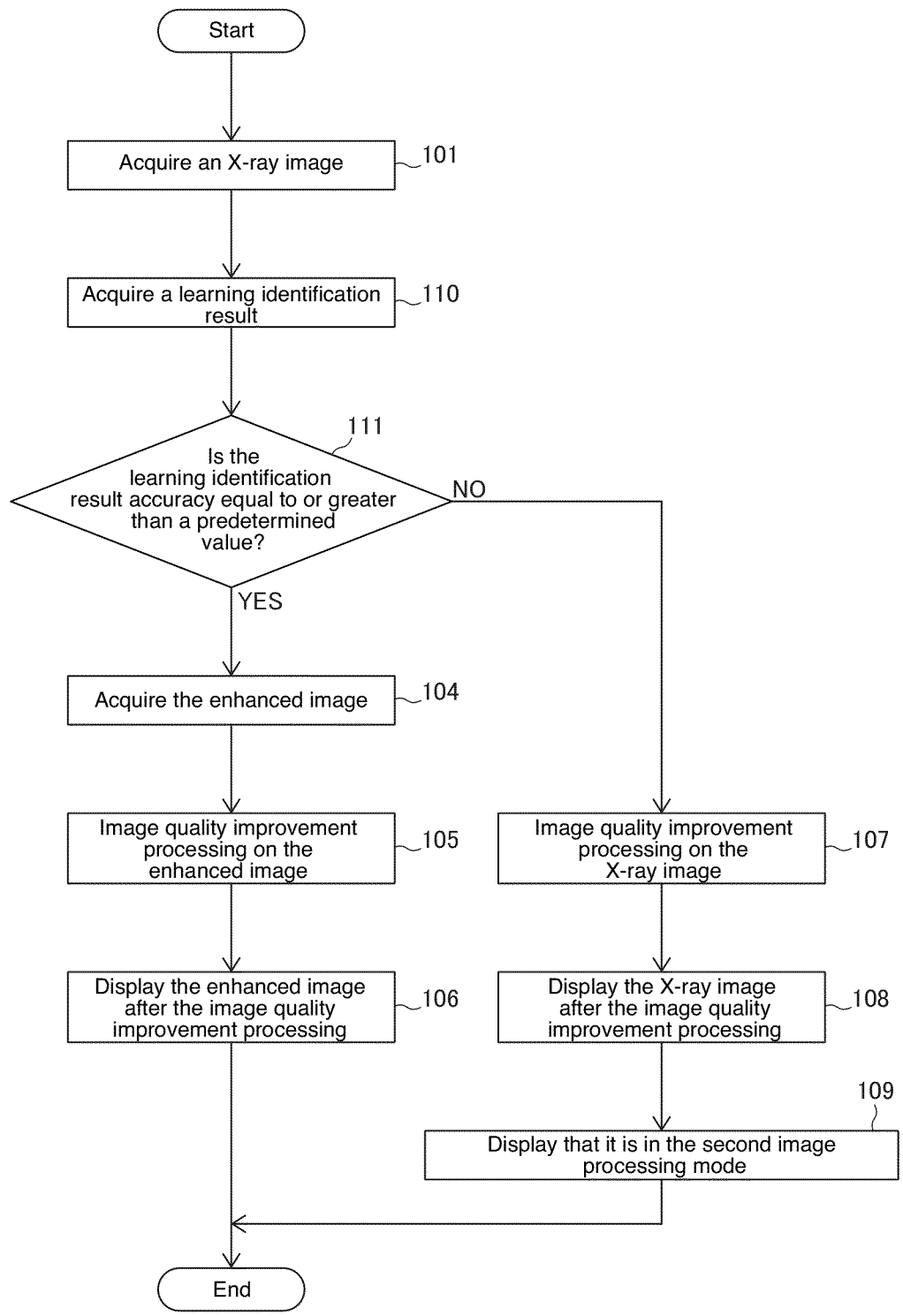
FIG. 8 is a flowchart describing image quality improvement processing according to a modification.

Next, the image quality improvement processing according to the modification will be described with reference FIG. 8. Note that the same processing as the image quality improvement processing by the above-described embodiment is assigned by the same reference numeral, and the detailed explanation thereof will be omitted.

In Step 101, the X-ray image acquisition unit 20 acquires an X-ray image 10.

In Step 110, the learning identification result utilization switching unit 120 acquires a learning identification result 7a. Specifically, the learning identification result utilization switching unit 120 acquires the accuracy of the learning identification result 7a.

In Step 111, the learning identification result utilization switching unit 120 determines whether the accuracy of the learning identification result 7a is equal to or greater than a predetermined threshold. When the accuracy of the learning identification result 7a is equal to or greater than the predetermined threshold, the processing proceeds to Step 104 to Step 106, and then ends. When the accuracy of the learning identification result 7a is smaller than the predetermined threshold, the processing proceeds to Step 107 to Step 109, and then ends.

Next, the image processing mode switching processing according to the modification will be described with reference to FIG. 9. Note that as for the same processing as that of the image processing mode switching processing according to the above-described embodiment, the same reference symbol is assigned, and the detailed description thereof will be omitted.

In Step 206, the learning identification result utilization switching unit 120 acquires the learning identification result 7a. Specifically, the learning identification result utilization switching unit 120 acquires the accuracy of the learning identification result 7a.

In Step 207, the learning identification result utilization switching unit 120 determines whether the accuracy of the learning identification result 7a is equal to or greater than a predetermined threshold. When the accuracy of the learning identification result 7a is equal to or greater than the predetermined threshold, the processing proceeds to Step 202 and Step 203, and then ends. Further, in a case where the accuracy of the learning identification result 7a is less than the predetermined threshold, the processing proceeds to Step 204 and then ends.

In the modification, as described above, the learning identification result utilization switching unit 120 is configured to switch between the first image processing mode and the second image processing mode based on the learning identification result 7a output from the learning model 7. With this, the first image processing mode and the second image processing mode are switched by the learning identification result 7a, and therefore, even in a case where, for example, the operator cannot grasp that the false detection of the device 80 has occurred, it is possible to switch between the first image processing mode and the second image processing mode. Consequently, it is possible to suppress the decrease in the visibility of the device 80 due to the learning identification result 7a regardless of the skill level of the user.

In the above-described embodiment, an example is shown in which the image quality improvement processing unit 22 performs the enhancement processing on the X-ray image 10 to acquire the enhanced image 11, but the present invention is not limited thereto. In the present invention, it may be configured, for example, to acquire the enhanced image 11 by the learning model by having the learning model learn to identify the device 80 and to emphasize the identified device 80.

Further, in the above-described embodiment, an example is shown in which the display control unit 24 displays that it is in the second image processing mode during the execution of the second image processing mode and does not display that it is in the first image processing mode during the execution of the first image processing mode, but the present invention is not limited thereto. For example, the display control unit may be configured to display that it is in the first image processing mode during the execution of the first image processing mode.

Further, in the above-described embodiment, an example is shown in which the X-ray fluoroscopic imaging apparatus 100 is provided with the first processor 2a and the second processor 2b, but the present invention is not limited thereto. For example, the X-ray fluoroscopic imaging apparatus may be configured to include only one processor. However, in a case where the X-ray fluoroscopic imaging apparatus is provided with only one processor, the identification processing of the device 80 by the target distribution learning identification unit increases the processing load on the processor. Therefore, the X-ray fluoroscopic imaging apparatus is preferably configured to include a first processor 2a and a second processor 2b.

Further, in the above-described embodiment, an example is shown in which the target distribution learning identification unit 21 performs the identifying processing of the device 80 appearing in the X-ray image 10 both in the first image processing mode and the second image processing mode, but the present invention is not limited thereto. For example, the target distribution learning identification unit may be configured to perform the identifying processing of the device 80 appearing in the X-ray image 10 only during the execution of the first image processing mode. That is, the target distribution learning identification unit may be configured not to perform the identifying processing of the device 80 appearing in the X-ray image 10 during the execution of the second image processing mode.

In the above-described embodiment, an example is shown in which the image quality improvement processing unit 22 performs the noise reduction processing as image quality improvement processing, but the present invention is not limited thereto. For example, the image quality improvement processing unit may be configured to perform the processing of improving the contrast of the X-ray image 10. The image quality improvement processing unit may perform any processing as long as the visibility of the device 80 appearing in the X-ray image 10 can be improved.

In the above-described embodiment, an example is shown in which the image quality improvement processing unit 22 performs the processing using a recursive filter as noise reduction processing, but the present invention is not limited thereto. For example, the image quality improvement processing unit may be configured to perform processing other than the processing using a recursive filter, such as, e.g., processing using a low-pass filter, as noise reduction processing. As long as the noise of the X-ray image 10 can be reduced, the image quality improvement processing unit may be configured to perform any processing.

Further, in the above-described embodiment, an example is shown in which the learning identification result utilization switching unit maintains the first image processing mode or the second image processing mode that is being executed even in a case where the imaging condition is changed, but the present invention is not limited thereto. For example, the learning identification result utilization switching unit may be configured to maintain the executing image processing mode even in a case where the imaging site is changed.

Further, in the above-described embodiment, an example is shown in which the learning identification result utilization switching unit is configured to maintain the first image processing mode or the second image processing mode that are being executed even in a case where the dose of X-rays is changed as an imaging condition, but the present invention is not limited thereto. For example, the learning identification result utilization switching unit may be configured to maintain the first image processing mode or the second image processing mode that are being executed even in a case where the imaging condition other than the dose of X-rays is changed, such as, e.g., changing the angle of the arm 1c.

Further, in the above-described embodiment, an example is shown in which the learning identification result utilization switching unit maintains the first image processing mode or the second image processing mode that is being executed even in a case where the imaging site or the imaging condition is changed, but the present invention is not limited thereto. For example, the learning identification result utilization switching unit may be configured to change to a normal image processing mode when the imaging site or the imaging condition is changed.

In the above-described embodiment, an example is shown in which the X-ray fluoroscopic imaging apparatus 100 is provided with the learning identification result utilization switching unit 23, but the present invention is not limited thereto. For example, the X-ray fluoroscopic imaging apparatus 100 may not be provided with the learning identification result utilization switching unit 23.

Further, in the above-described embodiment, an example is shown in which the X-ray image acquisition unit 20 acquires the X-ray image 10 as a moving image, and the image quality improvement processing unit 22 performs the image quality improvement processing on the X-ray image 10 as a moving image in either the first image processing mode or the second image processing mode, but the present invention is not limited thereto. For example, it may be configured such that the X-ray image acquisition unit acquires the X-ray image as a still image, and the image quality improvement processing unit performs the image quality improvement processing on the X-ray image as a still image in either the first image processing mode or the second image processing mode.

In the above-described embodiment, an example is shown in which the switching button 4a is displayed on the display unit 3 as a button on a GUI, but the present invention is not limited thereto. For example, the switching button 4a may be included in the input reception unit as a physical button.

Further, in the above-described embodiment, an example is shown in which the image quality improvement processing unit 22 improves the image quality of the device 80 appearing in the X-ray image 10, but the present invention is not limited to this. For example, the image quality improvement processing unit 22 may be configured to perform image quality improvement on the blood vessel or the bone appearing on the X-ray image 10 as a target.

Further, in the above-described embodiment, an example is shown in which the learning model 7 identifies at least one of a catheter, a stent, and a guidewire as the device 80, but the present invention is not limited thereto. For example, the learning model may be configured to identify, as a device, a coil for use in the treatment of, e.g., an aneurysm. If it is a device used while being imaged by an X-ray fluoroscopic imaging apparatus, any devices that can be identified by a learning model may be used.

Aspect

It will be appreciated by those skilled in the art that the above-described exemplary embodiments are illustrative of the following aspects.

(Item 1)
An X-ray fluoroscopic imaging apparatus comprising:
an imaging unit including an X-ray source for irradiating a subject with X-rays and an X-ray detector for detecting X-rays irradiated from the X-ray source;
an X-ray image acquisition unit configured to acquire an X-ray image captured by the imaging unit;
a target distribution learning identification unit configured to output distribution of a target appearing in the X-ray image using a trained learning model;
an image quality improvement processing unit configured to perform image quality improvement processing for improving image quality of the X-ray image; and
a display unit configured to display the X-ray image,
wherein the image quality improvement processing unit is configured to switch between a first image processing mode for performing the image quality improvement processing on the X-ray image using a learning identification result by the target distribution learning identification unit and a second image processing mode for performing the image improvement processing mode on the X-ray image without using the learning identification result.

(Item 2)
The X-ray fluoroscopic imaging apparatus as recited in the above-described Item 1,
wherein the image quality improvement processing includes at least noise reduction processing, and
wherein the image quality improvement processing unit is configured to perform,
in the first image processing mode using the learning identification result, the noise reduction processing on an enhanced image in which enhancement processing of the target in the X-ray image has been performed, and
in the second image processing mode not using the learning identification result, the noise reduction processing on the X-ray image in which the enhancement processing has not been performed.

(Item 3)
The X-ray fluoroscopic imaging apparatus as recited in the above-described Item 1 or 2, further comprising:
a display control unit configured to cause
the display unit to display that it is in the second image processing mode together with the X-ray image during execution of at least the second image processing mode, and
the display unit not to display that it is in the first image processing mode during execution of the first image processing mode.

(Item 4)
The X-ray fluoroscopic imaging apparatus according to any one of the above-described Items 1 to 3, further comprising:
a learning identification result utilization switching unit configured to switch whether the learning identification result by the target distribution learning identification unit is used.

(Item 5)
The X-ray fluoroscopic imaging apparatus as recited in the above-described Item 4,
wherein the learning identification result utilization switching unit is configured to maintain the first image processing mode or the second image processing mode that is being executed, even in a case where at least one of an imaging site and an imaging condition is changed.

(Item 6)
The X-ray fluoroscopic imaging apparatus as recited in the above-described Item 4 or 5, further comprising:
an input reception unit configured to accept an operation input by an operator,
wherein the learning identification result utilization switching unit is configured to switch between the first image processing mode and the second image processing mode based on an input by the input reception unit.

(Item 7)
The X-ray fluoroscopic imaging apparatus as recited in any one of the above-described Items 4 to 6,
wherein the learning identification result utilization switching unit is configured to switch between the first image processing mode and the second image processing mode based on the learning identification result output from the learning model.

(Item 8)
The X-ray fluoroscopic imaging apparatus as recited in any one of the above-described Items 4 to 7, comprising:
a first processor including the X-ray image acquisition unit, the image quality improvement processing unit, and the learning identification result utilization switching unit,
a second processor provided separately from the first processor, the second processor including the target distribution learning identification unit,
wherein the X-ray image acquisition unit is configured to acquire the X-ray image as a moving image, and
wherein the target distribution learning identification unit is configured to perform processing of identifying the target both in the first image processing mode and in the second image processing mode.

(Item 9)
The X-ray fluoroscopic imaging apparatus as recited in the above-described Item 2,
wherein the image quality improvement processing unit is configured to perform, as the noise reduction processing, at least processing using a recursive filter that adds a pixel value of a predetermined pixel in each frame of the X-ray image.

(Item 10)

The X-ray fluoroscopic imaging apparatus as recited any one the above-described Items 1 to 9,
wherein the target includes at least any one of a stent, a guidewire, a catheter, a blood vessel, and a bone appearing in the X-ray image.

DESCRIPTION OF SYMBOLS

1: Imaging unit
1a: X-ray source
1b: X-ray detector
2a, 12a: First processor
2b: Second processor
3: Display unit
4: Input reception unit
7: Learning model
7a: Learning identification result
10, 10a, 10b: X-ray image
11, 11a, 11b: Enhanced image
20: X-ray image acquisition unit
21: Target distribution learning identification unit
22: Image quality improvement processing unit
23, 120: Learning identification result utilization switching unit
24: Display control unit
80: Device (target)
100, 200: X-ray fluoroscopic imaging apparatus

The invention claimed is:

1. An X-ray fluoroscopic imaging apparatus comprising:
an imaging unit including an X-ray source for irradiating a subject with X-rays and an X-ray detector for detecting X-rays irradiated from the X-ray source;
an X-ray image acquisition unit configured to acquire an X-ray image captured by the imaging unit;
a target distribution learning identification unit configured to output distribution of a target appearing in the X-ray image using a trained learning model;
an image quality improvement processing unit configured to perform image quality improvement processing for improving image quality of the X-ray image; and
a display unit configured to display the X-ray image,
wherein the image quality improvement processing unit is configured to switch between a first image processing mode for performing the image quality improvement processing on the X-ray image using a learning identification result by the target distribution learning identification unit and a second image processing mode for performing the image improvement processing mode on the X-ray image without using the learning identification result.

2. The X-ray fluoroscopic imaging apparatus as recited in claim 1,
wherein the image quality improvement processing includes at least noise reduction processing, and
wherein the image quality improvement processing unit is configured to perform,
in the first image processing mode using the learning identification result, the noise reduction processing on an enhanced image in which enhancement processing of the target in the X-ray image has been performed, and
in the second image processing mode not using the learning identification result, the noise reduction processing on the X-ray image in which the enhancement processing has not been performed.

3. The X-ray fluoroscopic imaging apparatus as recited in claim 1, further comprising:
a display control unit configured to cause
the display unit to display that it is in the second image processing mode together with the X-ray image during execution of at least the second image processing mode, and
the display unit not to display that it is in the first image processing mode during execution of the first image processing mode.

4. The X-ray fluoroscopic imaging apparatus according to claim 1, further comprising:
a learning identification result utilization switching unit configured to switch whether the learning identification result by the target distribution learning identification unit is used.

5. The X-ray fluoroscopic imaging apparatus as recited in claim 4,
wherein the learning identification result utilization switching unit is configured to maintain the first image processing mode or the second image processing mode that is being executed, even in a case where at least one of an imaging site and an imaging condition is changed.

6. The X-ray fluoroscopic imaging apparatus as recited in claim 4, further comprising:
an input reception unit configured to accept an operation input by an operator,
wherein the learning identification result utilization switching unit is configured to switch between the first image processing mode and the second image processing mode based on an input by the input reception unit.

7. The X-ray fluoroscopic imaging apparatus as recited in claim 4,
wherein the learning identification result utilization switching unit is configured to switch between the first image processing mode and the second image processing mode based on the learning identification result output from the learning model.

8. The X-ray fluoroscopic imaging apparatus as recited in claim 4, comprising:
a first processor including the X-ray image acquisition unit, the image quality improvement processing unit, and the learning identification result utilization switching unit,
a second processor provided separately from the first processor, the second processor including the target distribution learning identification unit,
wherein the X-ray image acquisition unit is configured to acquire the X-ray image as a moving image, and
wherein the target distribution learning identification unit is configured to perform processing of identifying the target both in the first image processing mode and in the second image processing mode.

9. The X-ray fluoroscopic imaging apparatus as recited in claim 2,
wherein the image quality improvement processing unit is configured to perform, as the noise reduction processing, at least processing using a recursive filter that adds a pixel value of a predetermined pixel in each frame of the X-ray image.

10. The X-ray fluoroscopic imaging apparatus as recited claim 1, wherein the target includes at least any one of a stent, a guidewire, a catheter, a blood vessel, and a bone appearing in the X-ray image.

* * * * *